United States Patent
Reuning et al.

[11] Patent Number: 5,871,467
[45] Date of Patent: Feb. 16, 1999

[54] POST-PYLORIC FEEDING TUBES

[75] Inventors: Frederick K. Reuning, Minnetonka, Minn.; Joseph M. Makowski, Kenneth Square, Pa.

[73] Assignee: Novartis Nutrition AG, Basel, Switzerland

[21] Appl. No.: 789,712

[22] Filed: Jan. 27, 1997

[51] Int. Cl.$^6$ .................................................. A61M 29/00
[52] U.S. Cl. ........................... 604/96; 604/54; 604/264; 604/280; 606/194
[58] Field of Search .................... 604/49, 54, 96, 604/97, 264, 270, 280; 606/192, 194; 128/772

[56] References Cited

U.S. PATENT DOCUMENTS

| | | | |
|---|---|---|---|
| 5,084,014 | 1/1992 | Picha et al. | 604/54 |
| 5,098,378 | 3/1992 | Piontek et al. | 604/49 |
| 5,100,384 | 3/1992 | McBrian | 604/99 |
| 5,112,310 | 5/1992 | Grobe | 604/175 |
| 5,139,486 | 8/1992 | Moss | 604/164 |
| 5,151,086 | 9/1992 | Duh et al. | 604/51 |
| 5,152,756 | 10/1992 | Quinn et al. | 604/270 |
| 5,167,627 | 12/1992 | Clegg et al. | 604/101 |
| 5,195,970 | 3/1993 | Gahara | 604/96 |
| 5,246,421 | 9/1993 | Saab | 604/96 |
| 5,259,367 | 11/1993 | Kirby et al. | 128/8 |
| 5,279,553 | 1/1994 | Winkler et al. | 604/53 |
| 5,281,200 | 1/1994 | Corso, Jr. et al. | 604/96 |
| 5,356,391 | 10/1994 | Stewart | 604/175 |
| 5,401,241 | 3/1995 | Delany | 604/43 |
| 5,509,899 | 4/1996 | Fan et al. | 604/96 |
| 5,527,280 | 6/1996 | Goelz | 604/96 |

*Primary Examiner*—Wynn Wood Coggins
*Assistant Examiner*—N. Kent Gring
*Attorney, Agent, or Firm*—Michael P. Morris, Esq.

[57] ABSTRACT

The present invention comprises a means for the manual placement of a jejunal feeding tube within the small intestine comprising the insertion of a single lumen tube within the jejunal feeding tube. The placement tube has an inflatable stylet located at the distal end thereof. Once the tube is placed in the stomach of the patient by way an ostomy, the placement device is passed through until the inflatable stylet exits the distal end of the feeding tube. A syringe is attached to the placement device using a luer hub stopcock and the inflatable stylet is inflated like a balloon with air, water or other suitable material. The surgeon may then manually grasp the inflated stylet and by moving it place the end of the feeding tube at the desired position in the small intestine. The stylet may then be deflated and the placement device withdrawn from the feeding tube once the tube is properly placed.

9 Claims, 2 Drawing Sheets

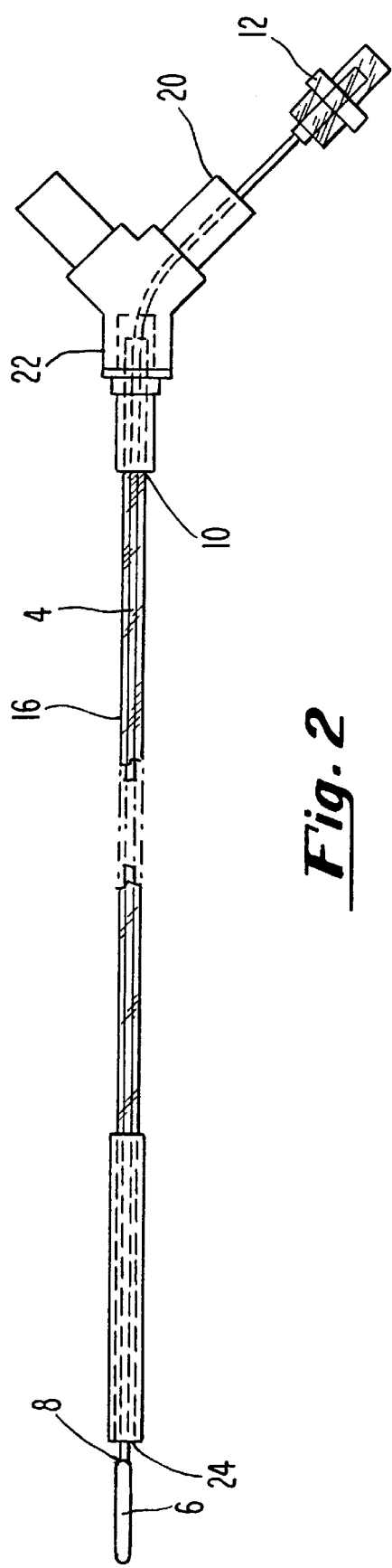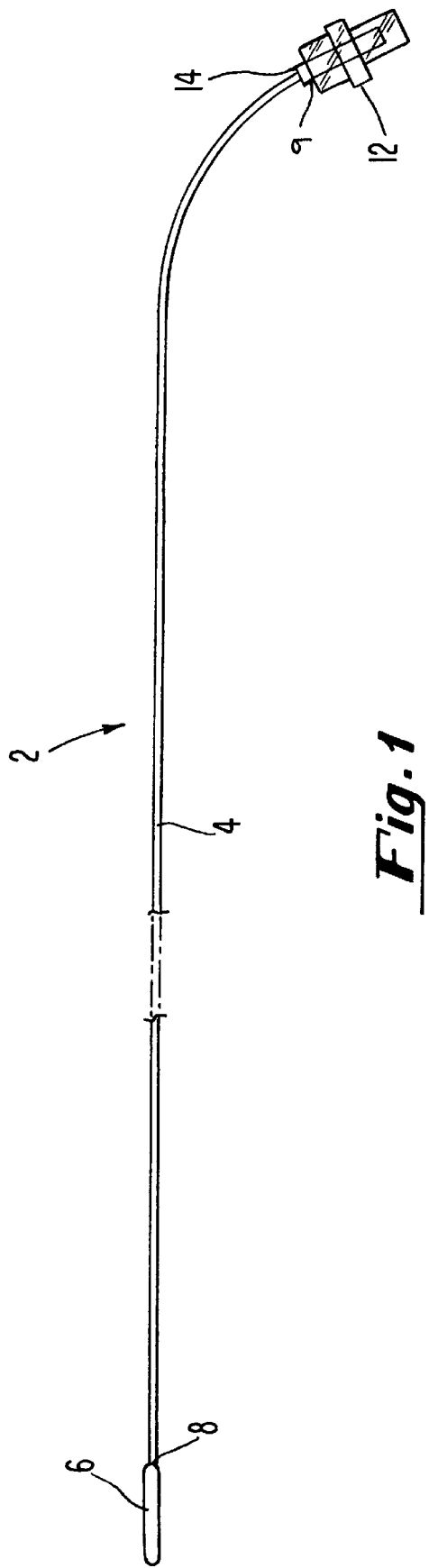

POST-PYLORIC FEEDING TUBES

FIELD OF THE INVENTION

The present invention relates generally to enteral feeding tubes used in the gastro-intestinal feeding of patients who are unable to swallow and digest food in the normal manner through the mouth, throat and stomach. More specifically, the present invention relates to improvements in the surgical placement and intubation of jejunal feeding tubes.

BACKGROUND OF THE INVENTION

The use of enteral feeding tubes which supply nutritional requirements of a patient directly to the stomach or other location in the digestive tract is often required when the patient for one reason or another cannot swallow, is unable to chew his or her food, or is unable to ingest enough food to meet the body's caloric requirements. Burn victims, the chronically ill, those inflicted with Alzheimer's disease and cancer patients are prime examples of these types of individuals. Enteral feeding usually employs a nasogastric tube to transport the liquid nutritional products through the nasal cavity and pharayrx and into the stomach.

Gastrostomy tubes may either be placed through the surgical creation of an ostomy while the patient is under general anesthesia or by means of percutaneous endoscopic gastrostomy (PEG) which involves a non-invasive creation of an opening or stoma in the stomach through the abdominal wall. The endoscope is passed down the throat until its terminus contacts the interior of the stomach. A needle with a stylet is inserted into the stomach wall until it passes therethrough. The stylet of the needle is retracted and a guidewire inserted through the cannula of the needle.

Using an endoscope, the end of the guidewire is grasped and pulled up through the throat. A permanent or primary gastrostomy tube is then put in place with its terminus within the stomach so as to form a direct enteral feeding conduit to the gastric system of the patient. However, there are often instances in which it is preferable to introduce the patient's nutritional requirements in the form of a liquid formula to the jejunum portion of the small intestine rather than the stomach. Some patients for example, when fed directly to the stomach, encounter a problem with such delivery known as reflux. In reflux, digested gastric residue is vomited up out the stomach and into the esophagus. Chronically ill or bed-ridden patients who are unable to swallow normally may inhale the gastric reflux inadvertently into the lungs resulting in asphyxiation or pneumonia. The tube itself can be forced out of the stomach as well. These situations in particular call for jejunal delivery of the nutritional formula.

It has been found in these instances that more efficatious feeding can be achieved if the feeding tube is passed through the pyloric area, and formula is passed directly into the patient's small intestine, rather than the patient's stomach. It has been further noted that when the feeding tube is installed so that the distal end is past the patient's pyloric valve, the tendency for the tube to be refluxed up to the esophagus is significantly reduced.

The jejunal feeding tube is introduced either through a surgically created ostomy or through the nasopharynxal passageway and passes through the stomach, the pylorus and then enters the small bowel, the duodenum and jejunum. Generally, with the patient sedated under general anesthesia, the surgeon guides the distal end of the tube through an ostomy to the jejunum. The lubricous and slippery environment of the lower abdomen however, makes grasping and manipulating the otherwise smooth and flexible tube considerably difficult.

U.S. Pat. No. 5,098,378 to Piontek et al. discloses and claims a replacement gastrostomy tube for jejunal feeding in which an expandable component of the tube is located at the distal end thereof. Fluid is passed through a fluid flow channel which enters the expandable component and inflates it like a balloon. In this fashion, the balloon and an adjacent retention device are pressed against the wall of the stomach, securing the feeding tube in the stoma.

U.S. Pat. No. 5,152,756 to Quinn et al. discloses an improved enteral feeding tube in which a bulbous extension member is attached to the distal end of the feeding tube. The extension is comprised of a stem portion that projects beyond the end of the tube parallel to the axis of the tube and forms a large spherical tip at its end. In this manner, the stem extension can be more easily grasped by forceps for surgical placement.

U.S. Pat. No. 5,100,384 to McBrian et al. discloses a device for percutaneous intubation in which the feeding tube comprises an inflatable lumen that expands as a water swellable foam material contained therein absorbs water from the gastro-intestinal cavity after intubation. A wire or suture loop is disposed at the terminal end of the feeding tube lumen for attachment to a wire used in pulling the tube through the esophagus and stomach during the intubation procedure.

U.S. Pat. No. 5,037,387 also to Quinn et al. discloses a method for positioning an enteral feeding tube within a patient's body and a tube for use therein comprising a flexible polyurethane tube and a rigid stem portion at the distal end thereof that forms an outlet from which the nutritional fluid flows. The stem itself ends in a spherical tip or ring which prevents the possibility of a puncture of the gastro-intestinal tract as the enteral feeding tube is pulled.

None of these prior art gastrostomy tubes provide an easy and effective means to enable the surgeon to quickly and safely place the end of the tube within the jejunum. Moreover, none of the prior art methods or devices allow the surgeon to safely locate and grasp the distal end of the feeding tube without posing a risk of injury to the organ walls and fascia. Nothing suggests a means whereby despite the slippery and lubricous environment of the gastro-intestinal tract, the tube can be firmly grasped and directed into the jejunum without the risk of getting caught within the pyloric valve or duodenum.

SUMMARY OF THE INVENTION

The present invention is an improved jejunal feeding tube wherein the distal end comprises a stylet with an inflatable balloon attached thereto which can be expanded during intubation. The balloon enables the surgeon through a laparotomy to palpate the tube as it is placed within the stomach or intestine through the tissue of these organs and enables the surgeon to easily position the distal end within the intestine. Once placed, the balloon is deflated so there is little risk of clogging the intestine or causing other injury.

BRIEF DESCRIPTION OF THE DRAWINGS

FIG. 1 is an overall view of the jejunal feeding tube placement device of the present invention.

FIG. 2 is a view of the device within a jejunal feeding tube with the stylet uninflated.

DETAILED DESCRIPTION OF THE INVENTION

Figure 3:
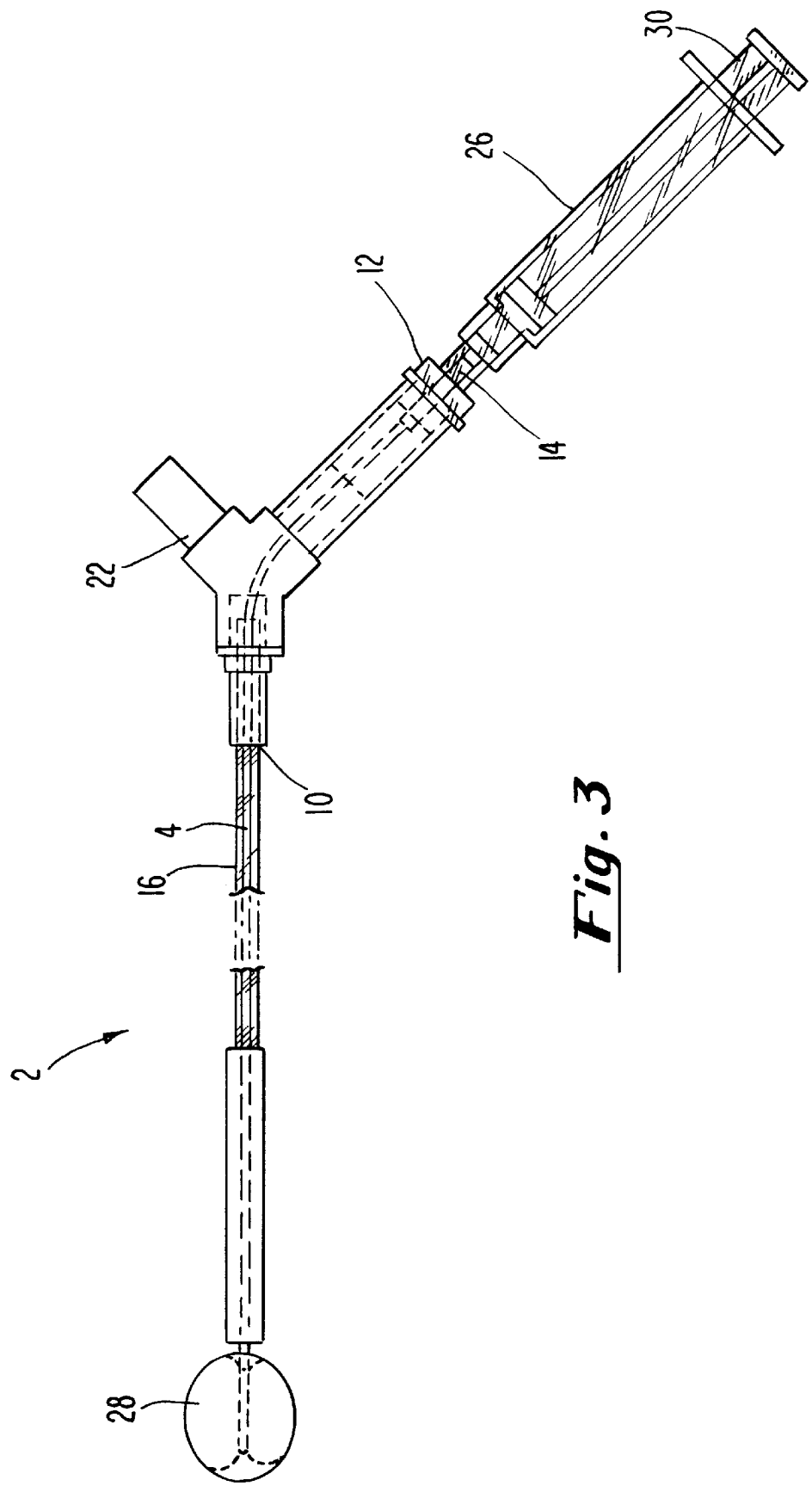
FIG. 3 is a view of the entire device within the feeding tube with the stylet balloon inflated.

The present invention comprises an improved post-pyloric feeding tube consisting of a device herein referred to as the stylet, which is intended to assist in the surgical laparotomy transgastric placement of a feeding tube such that the feeding tip of the tube is positioned in the small intestine. The assistance is provided by temporarily expanding an inflated balloon at the tip of the feeding tube so that the surgeon may manually palpate the tip and manipulate it post-pylorically to the extent afforded by the length of the tube. Some devices on the market currently have permanently attached balloons which are used in a similar manner. However, these balloons remain inflated for retention purposes so as to keep the tube secured to the wall of the stomach or other gastro-intestinal surface.

The device consists of a single lumen tube with an inflatable balloon within a stylet on one end and stopcock on the other end. The tubing material itself is sufficiently stiff to allow placement of the stylet down the lumen of a feeding tube by pushing from the feeding tube's connector end. When the tip of the stylet has been extended past the end of the feeding tube, the balloon may be inflated using a syringe or other air/water pump device through the stopcock which is then closed in order to keep the balloon inflated. Gentle traction may be placed on the stylet to position the balloon at the tip of the feeding tube. Thus, the end of the feeding tube may be located by palpating the balloon.

Using a removable device for feeding tube positioning allows the feeding tube to have a larger internal diameter for fluid flow since the need for a second lumen (inflation channel) to inflate the balloon is obviated. This is an advantage because the feeding tube is less prone to clogging and there is no need to maintain an inflated balloon/channel.

In use, the patient is anesthetized and a surgical laparotomy is performed as is known in the art. The balloon stylet and jejunal feeding tube of the present invention are lubricated with a pharmaceutically acceptable water soluble lubricant and the stylet is inserted into the stomach via the gastrostomy. Once the tube is in the stomach, the distal tip and stylet are grasped by the surgeon and are manually guided through the stomach past the pylorus and into the duodenum. The stylet balloon is then inflated with approximately 4.0 ccs. of water injected from a syringe that is inserted into the stopcock at the upper end of the feeding tube.

The surgeon can then manually manipulate the stylet by grasping the inflated balloon and moving the feeding tubes tip and positioning it in the distal duodenum or proximal jejunum of the small intestine. Once the tip is so positioned, the balloon can be deflated and the stylet removed.

Referring now to FIG. 1, the jejunal feeding tube placement device (2) of the present invention comprises a single, semi-flexible lumen tube (4) consisting of semi-rigid PVC plastic or other like material. An inflatable balloon (6) whose lumen is contiguous with that of the tube (4) is attached to the distal end (8) of the tube. At the proximal or opposite end of the tube (9) is a stopcock (12) comprised of clear, rigid plastic with a central bore (14) within which the flexible tube (4) is inserted. The lumen of the bore (14) of the stopcock (12) then is contiguous with that of the tube (4) and balloon (6) and thereby provides access thereto.

Referring now to FIG. 2, the intestinal tube placement device (2) is shown in cross-section within an intestinal feeding tube (16) with the placement stylet tip (6) uninflated. The flexible tube portion (4) of the placement device (2) is fed through the lumen of the feeding tube (16) as the diameter of the stylus (6) and semi-flexible tube (4) is less than that of the feeding tube. The stylet (6) is initially inserted in one of the openings (20) of the dual or multi-port feeding manifold (22) and is threaded or pushed through the length of the tube (16) after the tube has been surgically placed in the patient. The device is pushed therethrough until the stylet's inflatable tip (6) exits the distal end (24) of the jejunal feeding tube (16). The tube and stylet are then placed within the stomach of the patient using a standard gastrostomy procedure.

Referring now to FIG. 3, the jejunal tube placement device (2) of the present invention is shown in cross-sectional view with the inflatable stylet tip (6) inflated. A standard syringe (26) is screwed onto or attached to the part of the bore (14) of the luer hub stopcock (12) at the proximal end of the semi-flexible tube (10) of the present invention. Approximately four (4) ccs. of water (air or some other neutral gas or liquid would also suffice) is injected by the syringe through the stopcock (12) into and through the lumen of the tube (4) until it reaches and fills the lumen of the inflatable balloon (6). Filling in this manner, the balloon (6) expands and is easily grasped by the surgeon within the stomach or intestine of the patient. Using this expanded stylet as a guide, the intestinal feeding tube is properly placed within the small intestine. Once this is accomplished, the stopcock (12) is opened and the piston portion (30) of the syringe (26) is withdrawn thereby drawing the water or fluid out of the inflated stylet (28) and through the semi-rigid tube (4). The stylet is now deflated to a diameter less than that of the lumen of the jejunal feeding tube (16) allowing for the complete removal of the placement device therefrom.

Whereas it is recognized that minor changes and variations can be made with respect to the functional design of the placement tube of the present invention, it is to be understood that to the extent that any such changes do not materially alter the design and function of the device, they are considered to fall within the spirit and scope of the invention as recited by the following claims.

What is claimed is:

1. An intestinal feeding tube assembly comprising an intestinal tube placement device and an intestinal feeding tube wherein the intestinal tube placement device comprises:
   a. a single lumen tube with a proximal and distal end; and
   b. a stopcock located at the proximal end thereof, and an inflatable balloon located at the distal end thereof that is in open communication with the single lumen tubes; wherein the placement device is insertable through the intestinal feeding tube.

2. The placement device of claim 1 wherein said stopcock is a luer hub type.

3. The placement device of claim 1 wherein said balloon is inflatable by a syringe attached a stopcock at the proximal end of the single lumen tube.

4. A method for the placement of an intestinal feeding tube having one or more lumens within the intestine of a human patient comprising:
   a. inserting said feeding tube within a patient's stomach and small intestine, wherein a lumen of said feeding tube contains an intestinal placement device which comprises a smaller single lumen tube with a proximal end and a distal end with a stopcock located at said proximal end and an inflatable balloon located at and in open communication with said distal end of said single lumen tube and wherein the distal end of said intestinal placement device protrudes from the distal end of said feeding tube;
   b. inflating said balloon;
   c. manually grasping the intestines of said patient proximal to said inflated balloon while said intestinal feeding tube is moved within the intestines of said patient;

d. manually placing said balloon and intestinal feeding tube at an appropriate location within the intestines;

e. deflating said inflated balloon; and f. removing said intestinal placement device from the said intestinal feeding tube.

5. The method of claim 4 wherein said balloon is inflated using a syringe removeably attached to the stopcock located at the proximal end of the single lumen tube.

6. The method claims 5 wherein the diameter of the inflated balloon is greater than the diameter of the intestinal feeding tube.

7. The method of claim 6 wherein the diameter of the deflated balloon is less than the diameter of the lumen of the intestinal feeding tube.

8. The method of claim 7 wherein said intestinal placement device is inserted within a lumen of said intestinal feeding tube by way of one opening of a multiple feed port attached to the proximal end of the intestinal tube.

9. The method of claim 8 wherein said stopcock is a luer hub type.

* * * * *